(12) United States Patent
Gweon et al.

(10) Patent No.: US 6,744,510 B2
(45) Date of Patent: Jun. 1, 2004

(54) ELLIPSOMETER AND PRECISION AUTO-ALIGNMENT METHOD FOR INCIDENT ANGLE OF THE ELLIPSOMETER WITHOUT AUXILIARY EQUIPMENT

(75) Inventors: Dae Gab Gweon, Taejon (KR); Sung Lim Park, Taejon (KR); Jae Wha Jeong, Taejon (KR)

(73) Assignee: Korea Advanced Institute of Science and Technology (KR)

( * ) Notice: Subject to any disclaimer, the term of this patent is extended or adjusted under 35 U.S.C. 154(b) by 178 days.

(21) Appl. No.: 10/040,372

(22) Filed: Jan. 9, 2002

(65) Prior Publication Data

US 2003/0128360 A1 Jul. 10, 2003

(51) Int. Cl.⁷ .................................................. G01J 4/00
(52) U.S. Cl. ....................................... 356/369; 356/364
(58) Field of Search ................................ 356/369, 368, 356/364, 445

(56) References Cited

U.S. PATENT DOCUMENTS

| 4,192,995 | A | * | 3/1980 | Anthon ..................... 250/338.1 |
| 5,485,271 | A | * | 1/1996 | Drevillon et al. ............ 356/491 |
| 5,598,269 | A | * | 1/1997 | Kitaevich et al. ........... 356/399 |
| 6,031,614 | A | * | 2/2000 | Michaelis et al. .......... 356/369 |

* cited by examiner

Primary Examiner—Frank G. Font
Assistant Examiner—Roy M. Punnoose
(74) Attorney, Agent, or Firm—Duane Morris LLP

(57) ABSTRACT

An ellipsometer for aligning incident angle comprising: a main frame shaping half circle and flat surface on which a plurality of grooves are radial and circumferential directionally carved; a specimen stage, which is installed at the groove-caved surface of the main frame, for tilting a specimen on a upper surface of the specimen stage with respect to horizontal direction and translating the specimen upward and downward; a polarizing unit, which is capable of fixing and moving on the groove-carved surface of the main frame, for polarizing a light from a light source and outputting the polarized light to the specimen, and moving on the groove-carved surface; and a light detecting unit, which is capable of fixing and moving on the groove-carved surface, for a reflection light from the specimen.

4 Claims, 20 Drawing Sheets

US 6,744,510 B2

ELLIPSOMETER AND PRECISION AUTO-ALIGNMENT METHOD FOR INCIDENT ANGLE OF THE ELLIPSOMETER WITHOUT AUXILIARY EQUIPMENT

FIELD OF THE INVENTION

The present invention is related to an ellipsometer and alignment method for the incident angle of the ellipsometer, and particularly to an ellipsometer which is capable of performing three steps and one corrective sub step and precisely and repeatedly measuring surface characteristic of a specimen by scanning the surface by varying the incident angles of the light to the specimen and detecting the reflecting light from the specimen, and precision auto alignment method for incident angle of the ellipsometer.

BACKGROUND OF THE INVENTION

It is well known that the ellipsometric method is one of the most accurate optical methods to study reflecting surfaces through the measurement of the optical constants of a material or thin-layer parameters.

However, it makes use of optical and mechanical components that are always prone to induce more or less important errors. In addition, the alignment relative to the incident and reflected light beams, always delicate, must not be altered by the rotation of some of the optical components. If this alignment is not accurate, a systematic error could be included in the ellipsometric measurements. Therefore, the incident angle of the light toward the specimen must be correctly aligned. Here, the process to correct the altered incident angle is called as "incident angle alignment", which comes from misalignments of components including the specimen.

Recently, some investigators have shown that many cases of angle-of-incidence dependence of optical constants of specula surfaces can be attributed to azimuthal misalignments.

FIG. 1 shows a schematic block diagram of a conventional ellipsometer. As shown in the drawing, the conventional ellipsometer comprises a polarizing unit 1 for inputting a light from a light source and polarizing the light, a specimen stage 4 for supporting a specimen thereon and letting the polarized light from the polarizing unit 1 be incident on the specimen, a detecting unit 3 for detecting the reflecting light from the specimen and analyzing the detected light, and a focusing microscopy 4 for adjusting the incident angle of the polarized light from the polarizing unit 1 to the specimen.

FIG. 2 shows a detailed view of FIG. 1. As shown in the Figure, the polarizing unit 1 includes a polarizer 1b polarizing the light from the light source and a modulator 1a modulating the polarized light from the polarizer 1b and outputting the modulated light to the specimen 4a. Also, the detecting unit 3 includes an analyzer 3a inputting the reflection light from the specimen 4a and analyzing its polarizing state, and a detector 3b changing the light from the analyzing light into an electrical signal. Here, the dashed line stands for an optical path when the components are in perfect alignment and the continuous lines denotes an optical path when they are in misalignment.

However, the incident angle is altered by the misalignments of the components as well as the specimen stage. Namely, according to the state of the specimen stage 4 and the position of the specimen 4a on the specimen stage 4, there are h translation error and α tilt angle error and β tilt angle error. The h translation error occurs when components such as the polarizing prism and the light source, are set and the α tilt angle error and β tilt angle error rise, ie, when a new specimen is put on the specimen stage. The α and β tilt angle errors and the h translation error of the specimen stage may arise because the dimension of the present specimen may differ from the previous.

When a specimen, for example $SiO_2$ (of 100 nm) Si, is on the specimen stage 4 and the incident angle of the light onto the specimen 4a is 70, the α and β tilt angle errors and translation error occurs in the process for the measurements of the specimen and their quantities are as below.

When the analyzer prism is misaligned by 3 tilt angle error and rotates for measurement, the spot also rotates and is partially blocked by the detector's entrance aperture. The trajectory of the spot when the analyzer prism rotates is shown in FIG. 3, which was embodied in a Cartesian coordinate system from the electrical signals converted from the detecting light. The light is totally received or partially received from the detector's entrance aperture. Here, the dashed circle, G1, is a trajectory of the detector's entrance aperture, G2 is the trajectory of the spots and G3 is a trajectory of moving the center of the focus according to the rotation of the detector.

Thus, the signal of detector changes according to the fraction of light that is arrived at detector through the entrance aperture, as shown in FIG. 4.

FIG. 4 shows graphs where the detector converts the reflected signal into an electrical signal when the analyzer prism is misaligned. Here, G4 is a trajectory drawn by the detected signal at the detector when the components are misaligned, G5 is a trajectory drawn by the detected signal when the components 25 are perfectly aligned, and G6 is a trajectory drawn by a fraction of light which has arrived at the detector through the entrance aperture. Here, a value of 1 for the fraction of light at the axis of the normalized signal magnitude indicates that the spot has totally arrived at detector through the entrance aperture, provided that the detector is not saturated. Thus, the signal of the detector is the product of the intensity and the fraction of light.

Meanwhile, the orientation angle error of analyzer is, 3 the film thickness is calculated as 95.31 m nm, that is a 4.79 nm thickness error. In this case, the alignment precision depends on the precision of manufacture and assemblage.

When exchanging a specimen, the tilt angle errors and translation error of the specimen stage may arise. Because the dimension of the currently putting specimen may differ from that of the previous one. The alpha tilt angle error does not alter the incident angle but both beta tilt angle error and translation error alter the incident angle. The beta tilt angle error and translation error are related by the geometry of system.

FIG. 5 shows a measurement error of the film thickness with tilt angle error of specimen stage, which is the same as the beta tilt angle error, and FIG. 6 shows a measurement error of the film thickness with translation error of specimen stage, which is geometrically related with translation error.

The measurement error was proportional to both β tilt angle error and h translation error. 1 Å measurement error of film thickness is due to each 0.022° tilt angle error and 80 μm translation error of the specimen stage. From these results and rule of thumb, the resolutions of the specimen stage should be higher than 0.0022° and 8 μm each for tilt and translation motion, for the purpose of assuring 1 Å precision of measurement.

However, the conventional ellipsometers must use auxiliary equipment such as a focusing microscopy and 3-axis specimen stage for alignment of incident angle, which makes the system expensive. Also, it is difficult to compensate for the misalignment of incident angle, thereby it may not accurately analyze the surface characteristic of a specimen and not provide the complete information obtained therefrom either.

Also, another conventional ellipsometer using step motors may easily align the spot at the center of the detector's aperture though, but it still has a translation error of specimen stage cause incident angle error.

SUMMARY OF THE INVENTION

The main object of the present invention is to provide an ellipsometer which is capable of supplying a various incident angles of light onto a specimen and easily aligning the incident angles of light using kinematic coupling.

Another object of the present invention is to provide an ellipsometer which is capable of supplying a various incident angles of light onto a specimen and easily aligning the incident angles of light using a 3-axis specimen stage and a detector outputting a signal.

Still another object of the present invention is to provide a 3 step auto-alignment algorithm for supplying a various incident angles of light onto a specimen and easily aligning the incident angles of light using a 3 axis specimen stage and a detector outputting a signal.

In order to achieve the object of the present invention, there is provided an ellipsometer for aligning incident angle, wherein the ellipsometer comprises: a main frame shaping half circle and flat surface on which a plurality of grooves are radial and circumferential directionally carved; a specimen stage, which is installed at the groove carved surface of the main frame for tilting a specimen on an upper surface of the specimen stage with respect to horizontal direction and translating the specimen upward and downward; a polarizing unit, which is movably positioned on the groove-carved surface of the main frame for polarizing a light from a light source and outputting the polarized light on the specimen,; and a light detecting unit, which is movably positioned on the groove-carved surface to receive light reflected from the specimen.

In order to achieve the object of the present invention, a precision auto alignment method is provided to align the incident angle of an ellipsometer, wherein the precision auto alignment method comprises the steps of: measuring tilt and translating angle errors according to incident angles of a polarizing unit; compensating each error by moving a light spot reflecting from the specimen onto a center of the detector's entrance aperture; calculating the tilt and translating angle errors by repeatedly performing the measuring and compensating steps above; and correctly aligning incident angle for the ellipsometer by adjusting the tilt and translating angles accordingly.

DESCRIPTION OF THE PREFERRED EMBODIMENTS

Figure 7:
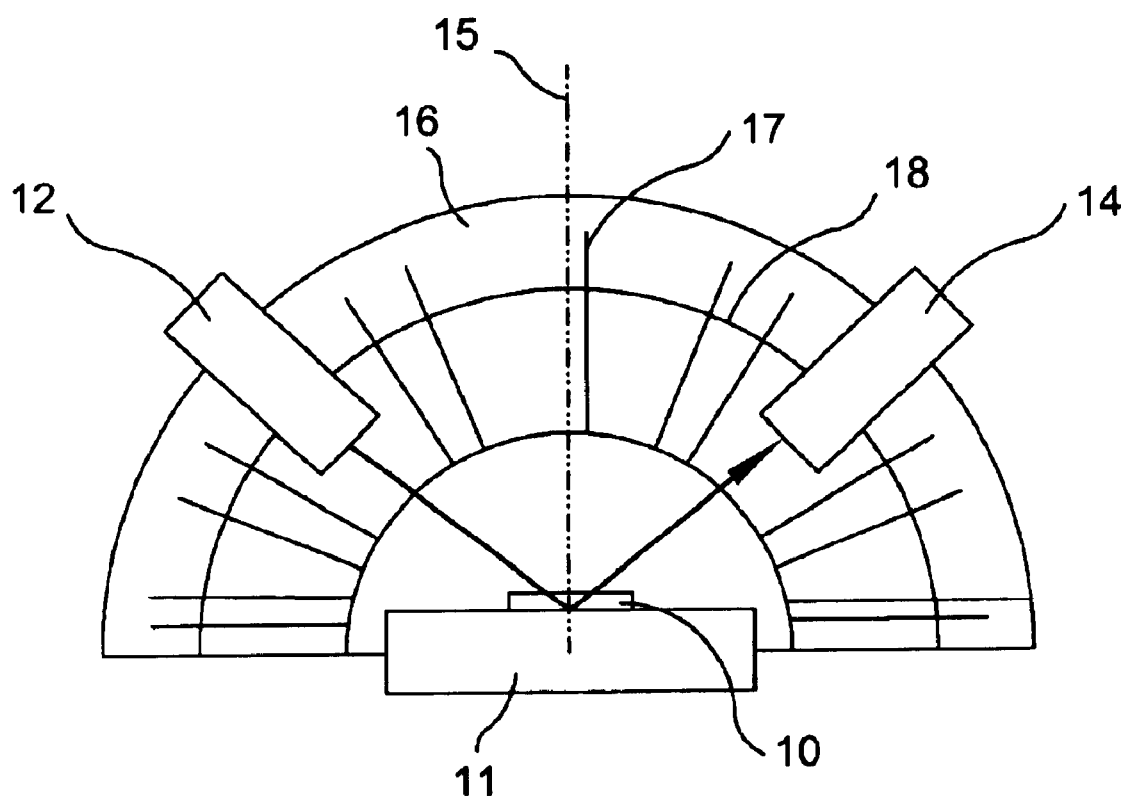
FIG. 7 shows an ellipsometer according to the present invention.

FIG. 7 shows an ellipsometer according to the present invention. As shown in the drawing, the ellipsometer comprises a specimen stage 11 for fixing a specimen 10 thereon and translating the specimen 10 upward and downward, a polarizing unit 12 for polarizing a light from a light source (not shown) and outputting the polarized light to the specimen 10, a light detecting unit 14 for a reflection light from the specimen 10, and a main frame 16 for fixing and supporting the components thereon.

Even though the polarizing unit 12 is illustrated in detail, we can easily appreciate that the polarizing unit 12 comprises a polarizer and a modulator like the conventional art. Similarly, the detecting unit comprises an analyzer and a photo detector. Further, the polarizing unit 12 and the detecting unit 14 are attached to each arm which can rotate with respect to the center of the main frame 16.

The main frame 16 shapes like a half-circle plane on which v-shape grooves are directionally carved. On one side of the main frame 16 a plurality of first grooves 17 are radial-directionally formed and a second groove 18 is formed parallel to the circumference direction with a certain radius. Here, the first grooves 17 are formed to be symmetric with respect to the vertical center axis 15 with a certain interval therebetween. Also, the positions and the shape of the grooves 17 and 18 must be accurately formed on the main frame 16, because the components outputting the light to the specimen and receiving the reflected light from the specimen are fixed or moved according to said positions and shapes.

Additionally, the material of the main frame includes ferrite components so that a magnet can attach thereon.

The specimen stage 11 can be tilted within a certain degree with respect to the horizontal plane and translated upward and downward. Thus it has three degree of freedom. Also, the upper surface center of the specimen stage 11 is preferably aligned to the center of the main frame 16, which is on the vertical center axis 15, for easily translating or tilting the specimen 10 thereon.

Figure 8:
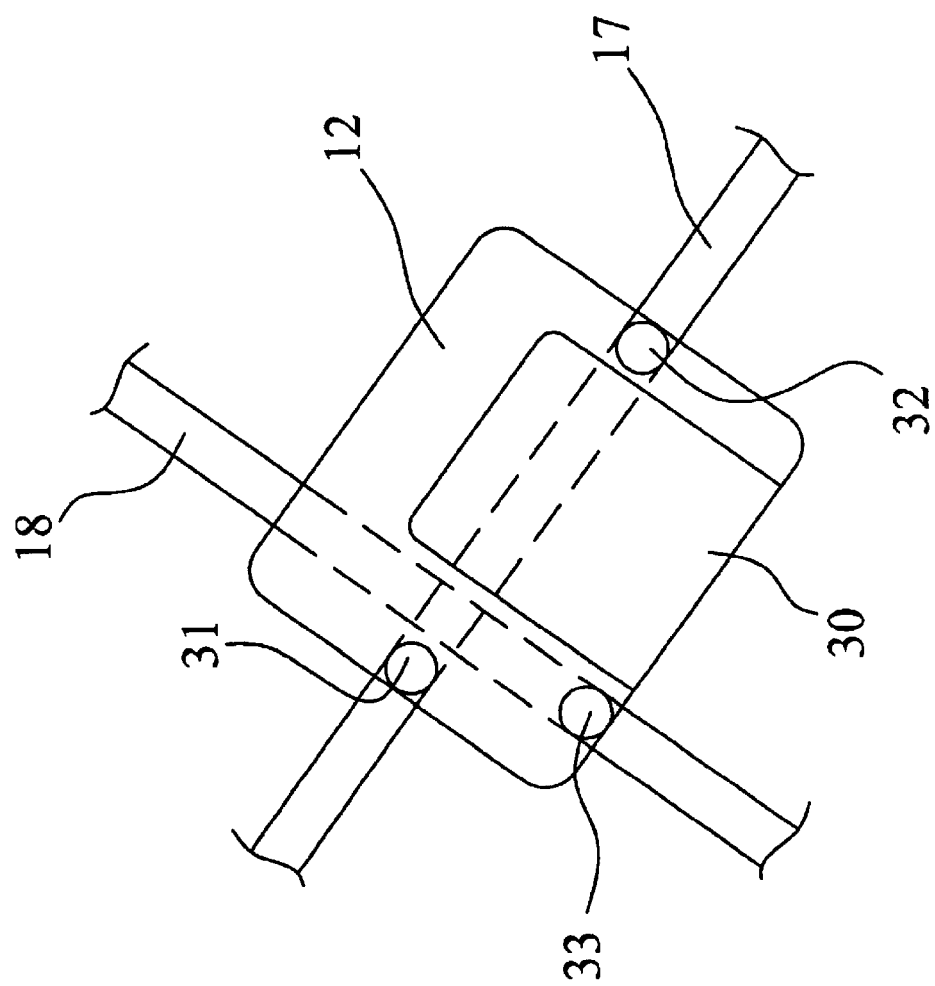
FIG. 8 shows a detailed view of the polarizing unit of the ellipsometer according to the present invention.

Meanwhile, the polarizing unit 12 of the ellipsometer according to the present invention as shown in FIG. 8, is fixed on one side of the main frame 16 by a permanent magnet 30 bonded under the polarizing unit 12 of which the surface faces to the surface of the main frame 16. Also, there are balls 31, 32 and 33 in the space between the surfaces of the polarizing unit 12 and the main frame 16. The balls 31 and 32 are on the grooves 17 so that the polarizing unit 12 is easily align to the direction of the center of the main frame 16 or the specimen 10 on the specimen stage 11. The ball 33 is on the groove 18 so that the polarizing unit 12 is easily moved to the next groove 17.

Similarly, the detecting unit 14 is aligned on the main frame 16 like the polarizing unit 12 mentioned above aligned except for its position. They are positioned to be symmetric with respect to the vertical center axis 15, thereby the incident angle and the reflection angle are the same.

The ellipsometer in accordance with the present invention mentioned above uses a 3 axis specimen stage and a signal detector that analyzes a surface characteristic of a specimen using a 3 step algorithm and one sub corrective algorithm as below:

The incident angle is essentially altered by the tilt angle error as well as the translation error of the specimen stage, which are caused by specimen. Thus, for perfect incident angle the tilt angle errors and the translation error of the specimen stage must be analyzed.

1) First of all, the corrective sub-step according to the present invention is proceeded as the spot is centered on the detector's entrance aperture by tilting the specimen stage. This sub-step consists of two sub-processes, which are an accessing process and centering process.

Figure 9A:
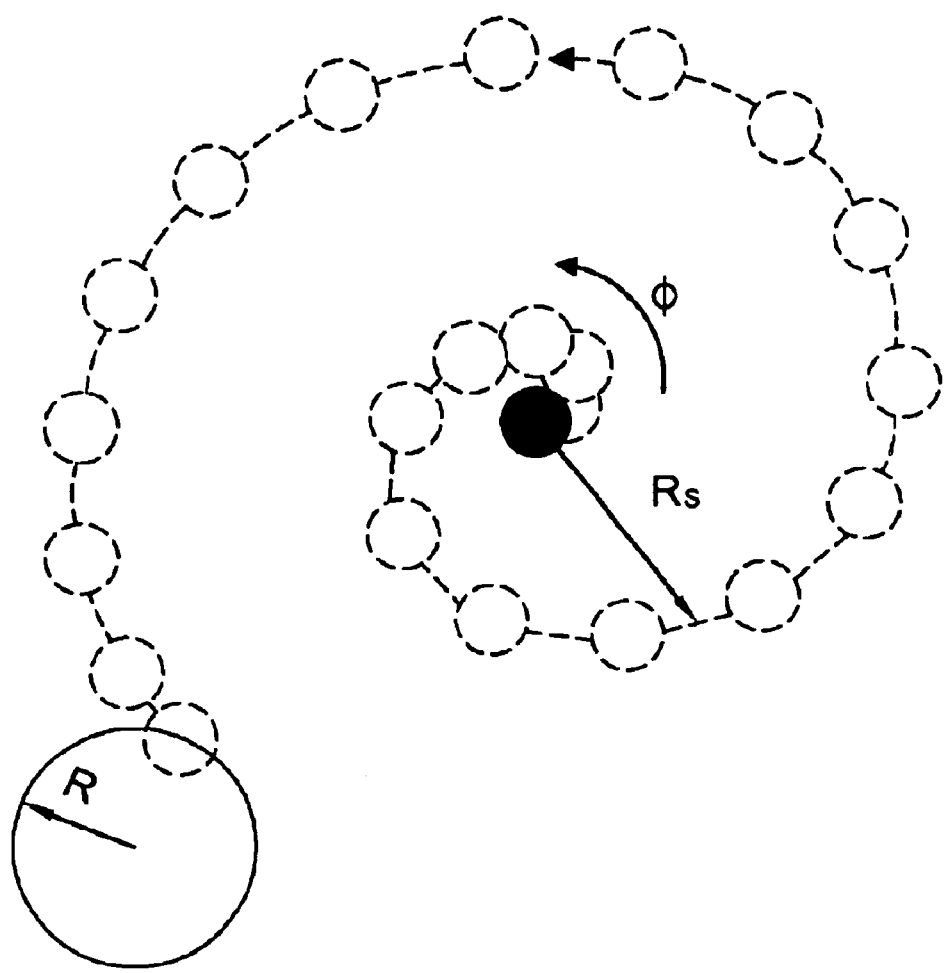
FIGS. 9A and 9B show an accessing process of the corrective sub-step according to the present invention.
Figure 9B:
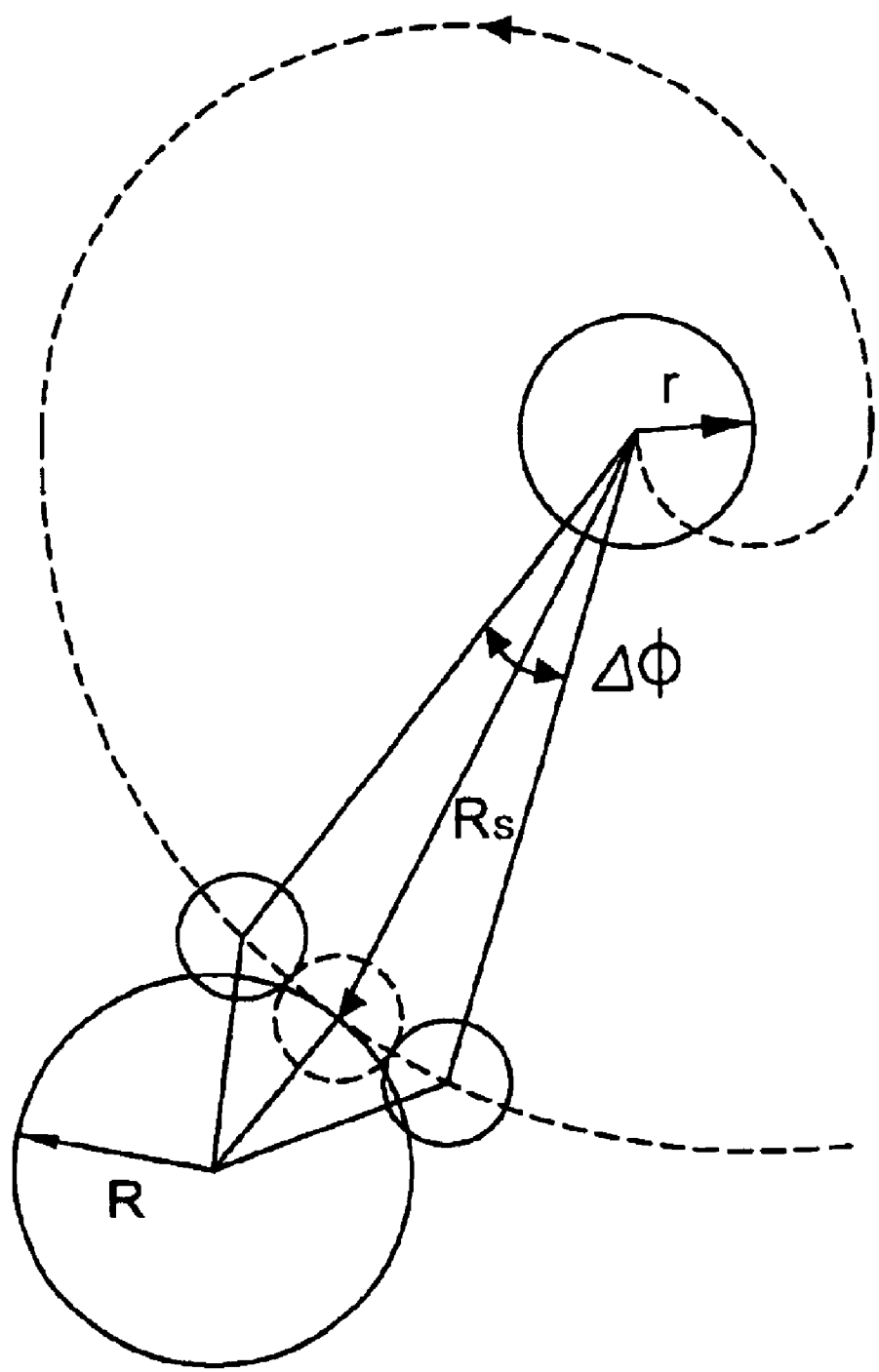

The definition of alignment in optical system is to maximize the light intensity at the detector. Once the detector can get any light intensity, the system can maximize the optical signal relatively easily. However, even when the light spot is away from entrance aperture of the detector, the system with auto-alignment ability should find its way to get the optical signal. We call this as an accessing process that has not been dealt with previously. In this process only two tilting motions are used without translational motion along the z axis. FIGS. 9A and B show the accessing trajectory (dashed line) of the reflected light spot in a spiral form of increasing radius. In order for the light to enter the detector's entrance aperture we had to carefully choose the parameters of the spiral. The radius ($R_s$) of the spiral is set to be (in FIGS. 9A and 9B)

$$R_s = (2R + r) \cdot \frac{\phi}{2\pi} \quad (1)$$

where R is the radius of the detector's entrance aperture, r is radius of the light spot, and $\phi$ is the azimuthal angle. The $\phi$ starts from zero and increases by the step size $\Delta\phi$ where $$\Delta\phi = 2\cos^{-1}\left(\frac{6R + r}{6R + 2r}\right) \quad (2)$$

as shown in FIG. 9B.

Figure 1:
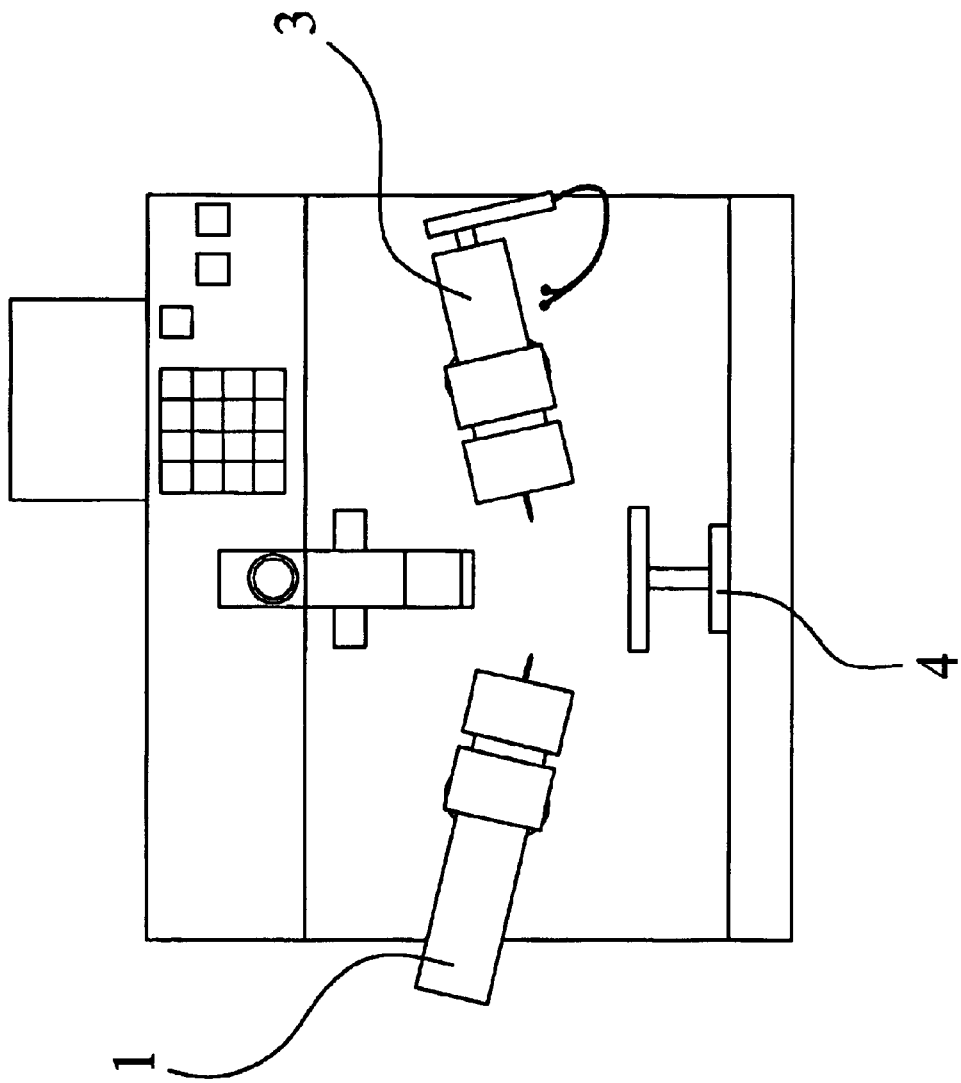
FIG. 1 shows a schematic block diagram of a conventional ellipsometer.
Figure 2:
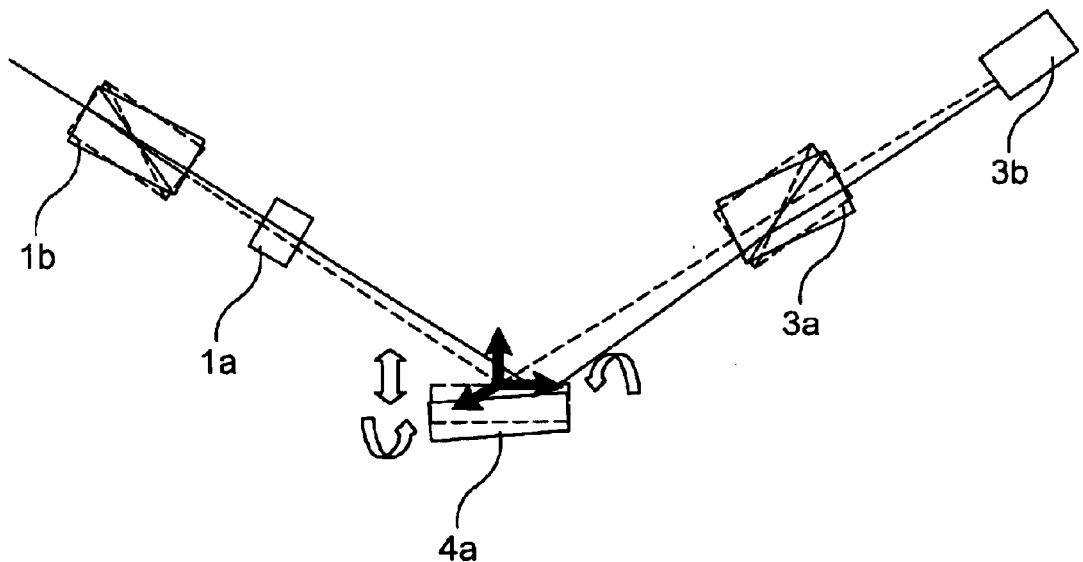
FIG. 2 shows a detailed view of FIG. 1.
Figure 3:
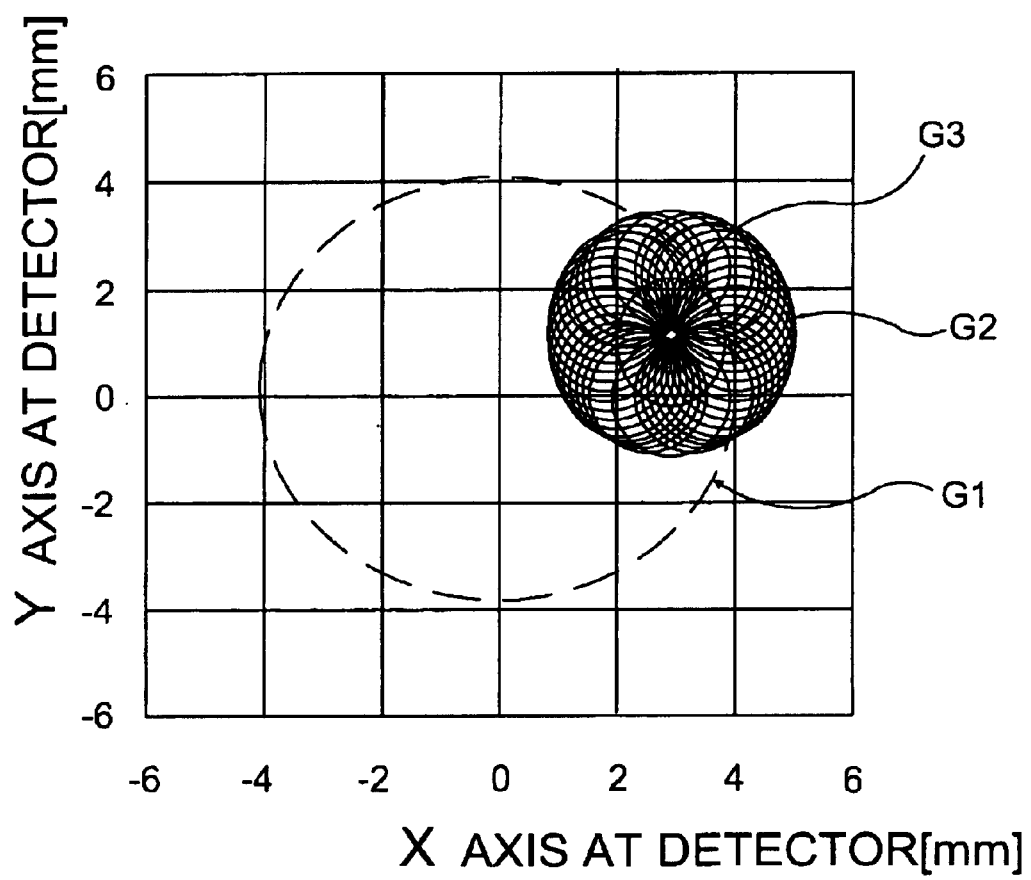
FIG. 3 shows trajectories of the light spot when the analyzer prism rotates.
Figure 4:
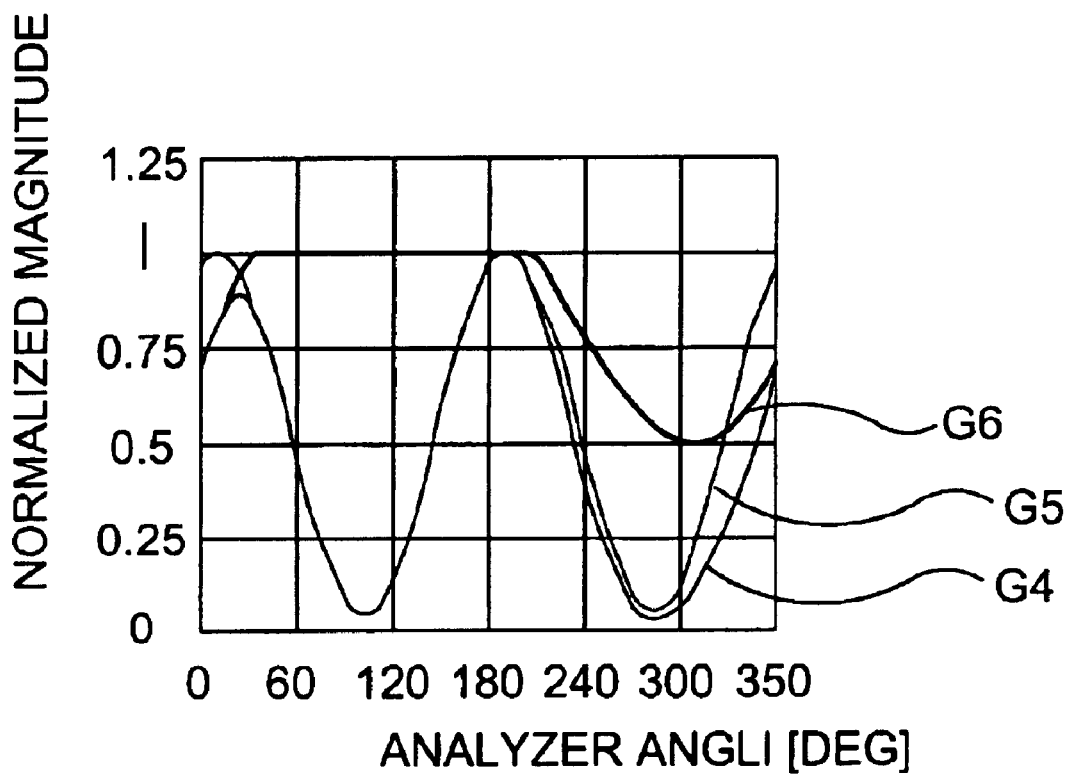
FIG. 4 shows graphs where the detector repeatedly converts the reflected signal into an electrical signal in a display when analyzer prism is misaligned.
Figure 5:
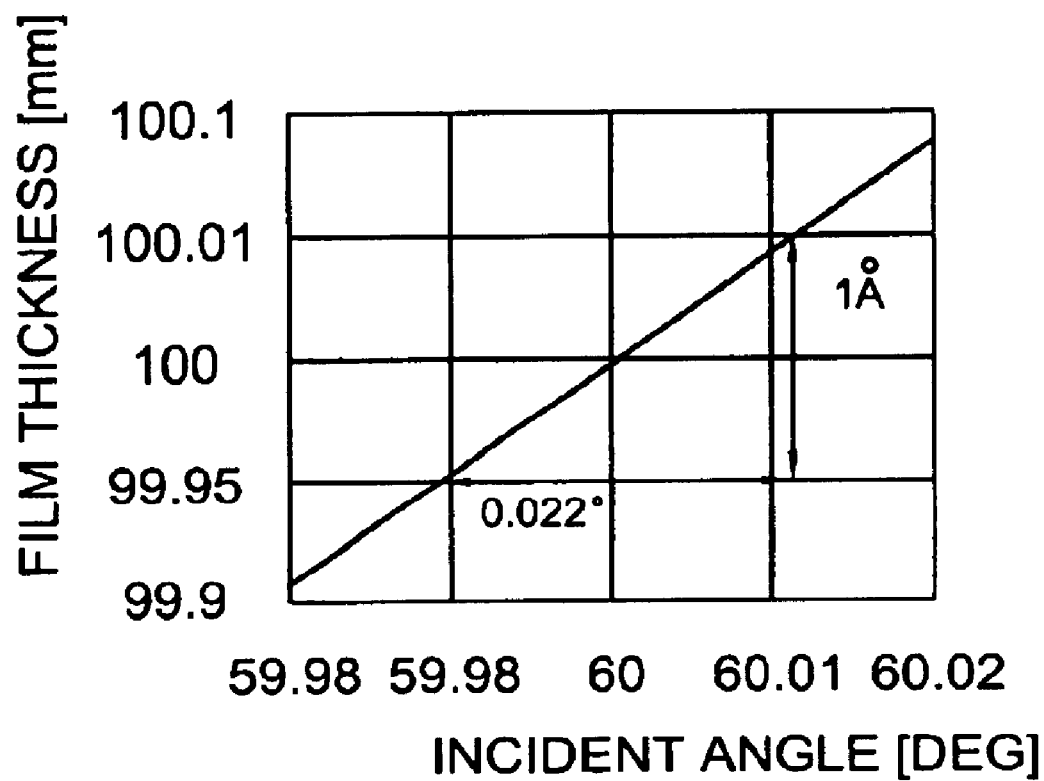
FIG. 5 shows a measurement error of the film thickness with tilt angle error of specimen stage, which is the same as the β tilt angle error.
Figure 6:
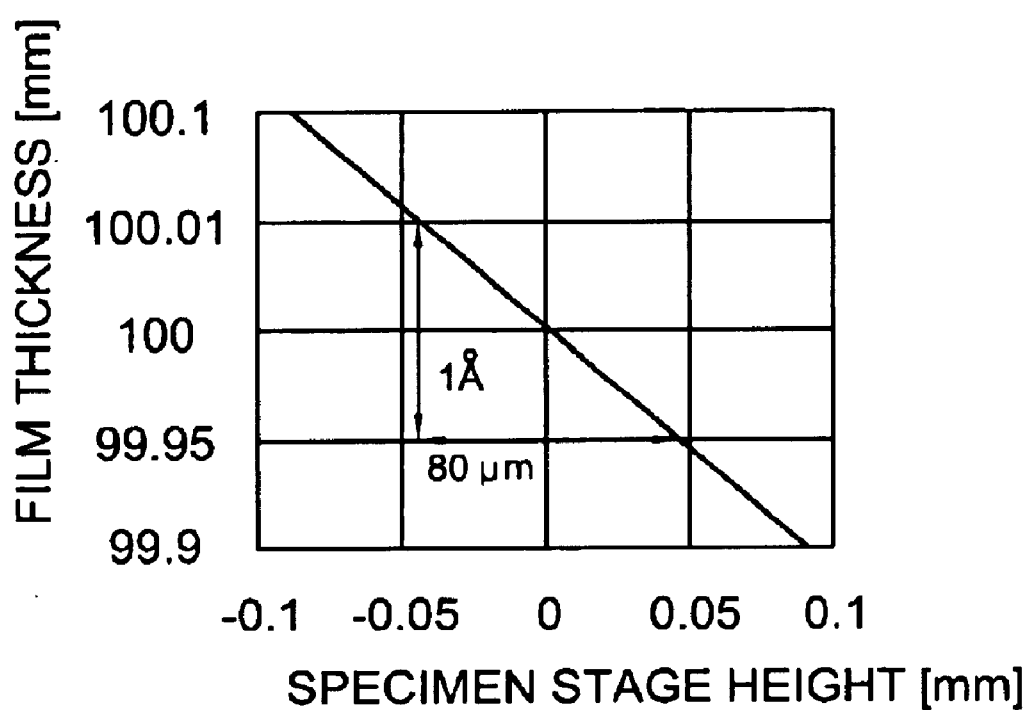
FIG. 6 shows a measurement error of the film thickness with translation error of specimen stage, which is geometrically related with translation error.
Figure 10A:
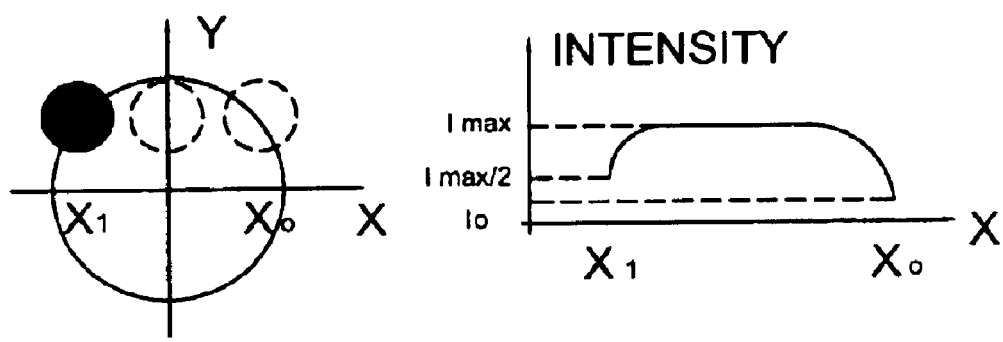
FIGS. 10A to 10C show centering processes of the corrective sub-step according to the present invention.
Figure 10B:
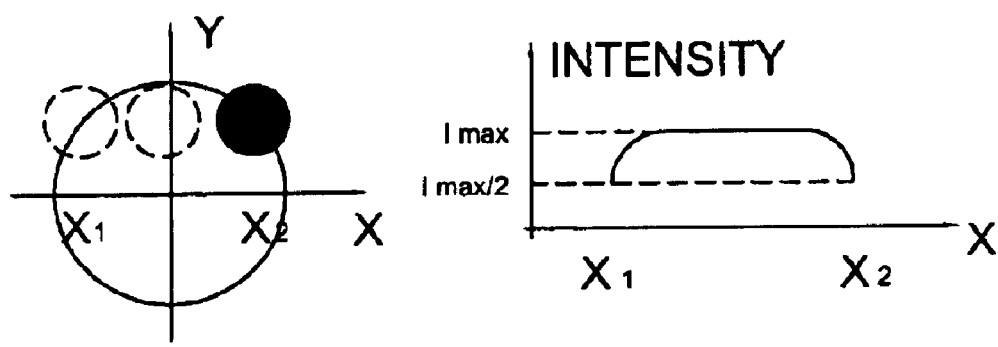
Figure 10C:
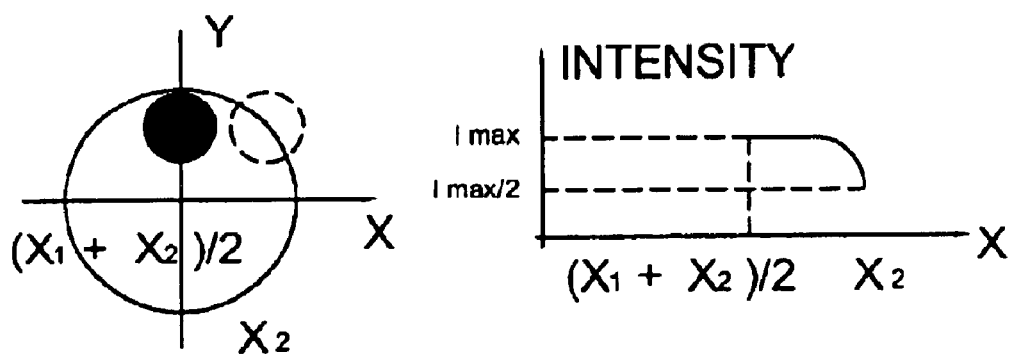

Once the detector finds any light signal, this accessing process stops, and the centering process shown in FIG. 10 starts. (Note that a new coordinate X Y in FIG. 10 is that at the detector's aperture, which is different from x y z at the specimen surface in FIG. 2.) The large bold circle represents the detector's aperture, while the small solid circle the light spot. Intensity of the detector signal is also shown together at right side of FIG. 10 for each corresponding position of the light spot. When the whole part of the light spot is inside the detector's aperture, the intensity signal has maximum, while the light spot is partially blocked by the edge of the aperture, the signal decreases. FIG. 10a shows that the initial position of light spot in the centering process would be around the edge of the detector's aperture after the accessing process, which is position $X_0$ in X-direction with light intensity signal as $I_0$. By changing β tilt angle we can move the light spot until its intensity signal passes the maximum (Imax) value, reaching the half of the maximum (Imax/2) where the position of light spot is $X_1$. (We have to add a few command lines in the centering algorithm to select the direction of movement. At the $X_0$ point, the change of light signal along positive and negative X-directions should be checked to select the right direction.) Once reaching at $X_1$ position, the spot moves in the reverse direction until it reaches the $X_2$ position where the light intensity is $I_{max}/2$ (FIG. 10B). Finally, the spot returns to the mid point of $X_1$ and $X_2$, which is the center position of the detector's aperture in X-direction (FIG. 10C). When the centering in X-direction is done, the alpha tilt angle error whose direction is perpendicular to the plane of incidence is completely removed because our specimen stage has independent movements along alpha and beta tilts as discussed above. For the Y direction, we repeat the same procedure by changing α tilt angle about x axis this time, finishing the centering process. It should be emphasized that in the centering process the detector's signal was not simply maximized. Instead, the light spot was set at the mid point between $I_{max}/2$, which is the center of detector's aperture. Note that even if the aperture size is smaller than that of the light spot, these accessing and centering processes still work.

FIGS. 9A and 9B shows the accessing process. Here, the large bold circle is the detector's aperture and the small solid circle is the reflected light spot.

FIG. 10 shows the centering process. Here, the left denotes a position of light spot at the detector's aperture and the right stands for a signal at the detector according to the position of light spot.

2) Meanwhile, the alpha tilt angle error is perpendicular to the incident plane, it can't give effect on incident angle and can be eliminated at any incident angle by tilting specimen stage. On the other hand, since the beta tilt angle error and translation error are parallel to the incident plane, these can give effect on incident angle. Unfortunately, both of them can't be eliminated at one incident angle. Therefore, two incident angles different from each other must be used to correct incident angle.

(1) The First Step

Figure 11:
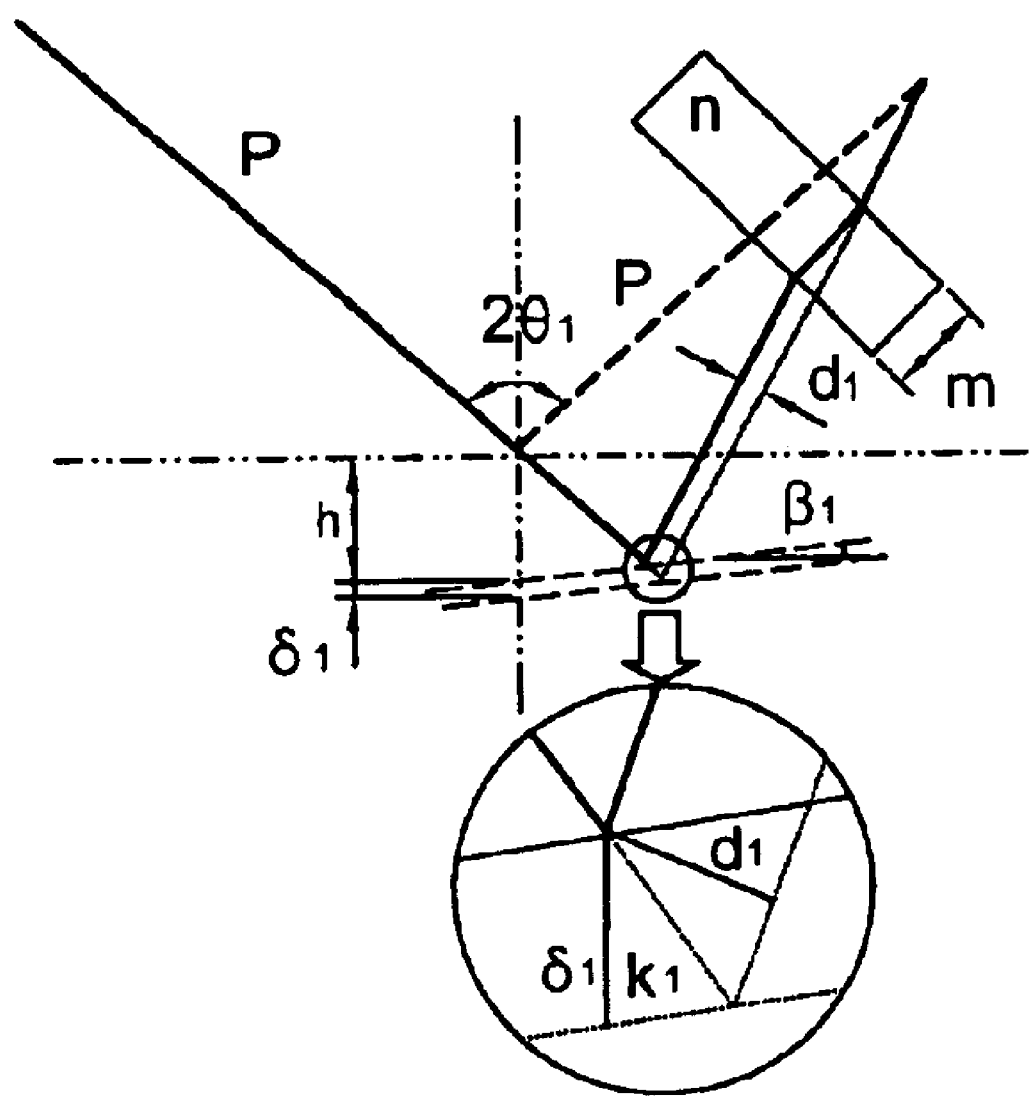
FIG. 11 shows an optical light path at the first step according to the present invention.

As shown in FIG. 11, the first incident angle may be arbitrary, but it should be different from the second. In this step, the polarizer and the analyzer arms are set at the first incident angle, and the spot is centered on the detector's entrance aperture by the corrective sub-step.

Here, the continuous bold line is optical light path when the specimen stage is misaligned and the dashed bold line is optical light path when the specimen stage is perfectly aligned.

Therefore, the optical light path is refracted and offset at the linear polarizing prism of the analyzer arm. The offset is $$d_1 = -m \cdot \left( \tan\beta_1 - \frac{\sin\beta_1}{\sqrt{n^2 - \sin^2\beta_1}} \right) \cos\beta_1 \quad (3)$$

where $\beta_1$ first tilt angle error of specimen stage, m thickness of linear polarizing prism, n refractive index of linear polarizing prism.

This offset of the optical light path causes apparent translation error of specimen stage.

$$\delta_1 = \frac{d_1}{2 \cdot \cos\beta_1 \cdot \sin(\theta_1 - \beta_1)} \quad (4)$$

where, $\theta_1$ first incident angle.

The relation between the tilt angle error and the translation error is $$h + \delta_1 = -\frac{\sin\beta_1}{\sin(\theta_1 - \beta_1)} p \quad (5)$$

where h is the translation error of specimen stage, and p is the distance between the specimen and the detector's entrance aperture.

(2) The Second Step

Figure 12:
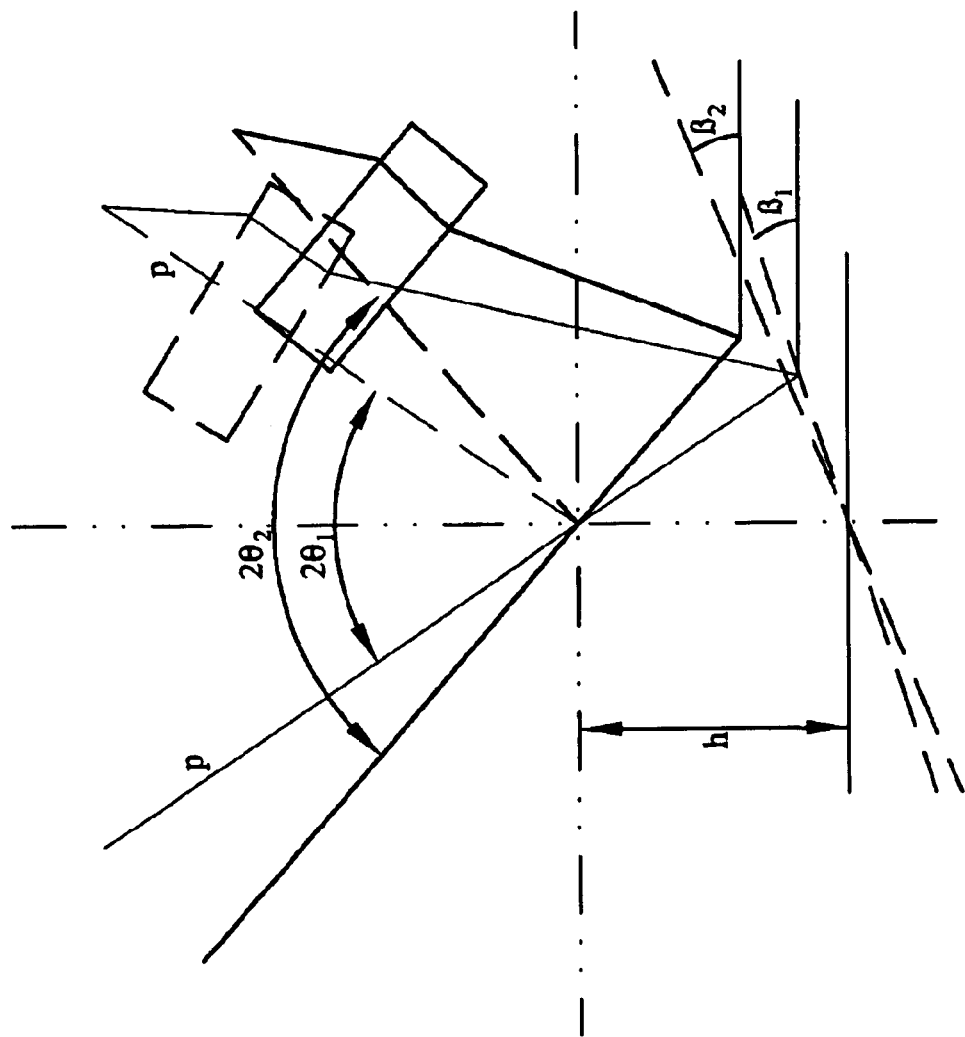
FIG. 12 shows an optical light path at the second step according to the present invention.

As shown in FIG. 12, the polarizer and the analyzer arms are set at the second incident angle. If there is translation error of the specimen stage, the spot must not be on the center of the detector's entrance aperture. The spot is centered on the detector's entrance aperture by the corrective sub-step.

Here, the continuous line is the real optical light path, but the dashed line is the ideal optical path. The optical light path is refracted and offset at the linear polarizing prism of analyzer arm. The offset is $$d_2 = -m \cdot \left( \tan\beta_2 - \frac{\sin\beta_2}{\sqrt{n^2 - \sin^2\beta_2}} \right) \cos\beta_2 \quad (6)$$

where $\beta_2$, is the second tilt angle error of specimen stage.

This offset of optical light path causes apparent translation error of the specimen stage.

$$\delta_2 = \frac{d_2}{2 \cdot \cos\beta_2 \cdot \sin(\theta_2 - \beta_2)} \quad (7)$$

where $\theta_2$ second incident angle.

The relation between the tilt angle error and the translation error is $$h + \delta_2 = -\frac{\sin\beta_2}{\sin(\theta_2 - \beta_2)} p \quad (8)$$

(3) The Third Step

Since thickness of specimens varies in everyday experiment, absolute $\beta_1$ value obtained by the first step is not meaningful. However, after the $2^{nd}$ step the difference between the first and second tilt angle errors can be computed to have absolute value as, $$\beta = \beta_2 - \beta_1. \quad (9)$$

Thus, $\beta_{32}$ can be expressed by $\beta_1$, which means that $h+\delta_2$ in Eq. (8) can also be expressed by only $\beta_1$. Since both the $\delta_1$, and the $\beta_2$ can be expressed by $\beta_1$, we can get the two unknown errors of h and $\beta_1$, from two equations of Eq. (5) and Eq. (8). Therefore, in the final $3^{rd}$ step, we can complete the alignment by moving specimen stage to the origin of the x-y-z coordinate of perfect alignment according to the calculated values of h and $\beta_1$.

In order to easily understand the operation of the ellipsometer according to the present invention, we will explain it below. In the experiment, the specification of the components is that; the light source is HeNe laser of 2 mW; the linear polarizing prism is a calcite (Glan Thompson) polarizer with an extinction ratio $<10^{-5}$ and ordinary refractive index 1.655; the linear polarizing prism is rotated by a hollow shaft step motor; the modulator is a 50 kHz photoelastic modulator (PEM-90, HINDS co.); the detector is a silicon photodiode; the accuracy of incident angle is lower than 0.0014° according to the manufacturing accuracy 5 μm; the specimen stage has one translation and two tilt motions, 60 nm resolution and 25 mm range for translation motion, $10^{-6}$ degree resolution and 20 degree range for tilt motions; the specimen is the Si bare wafer; the first and second incident angles are 30° and 70°, respectively; each component and optical path in 3-dimensions are represented in HTM.

Figure 13:
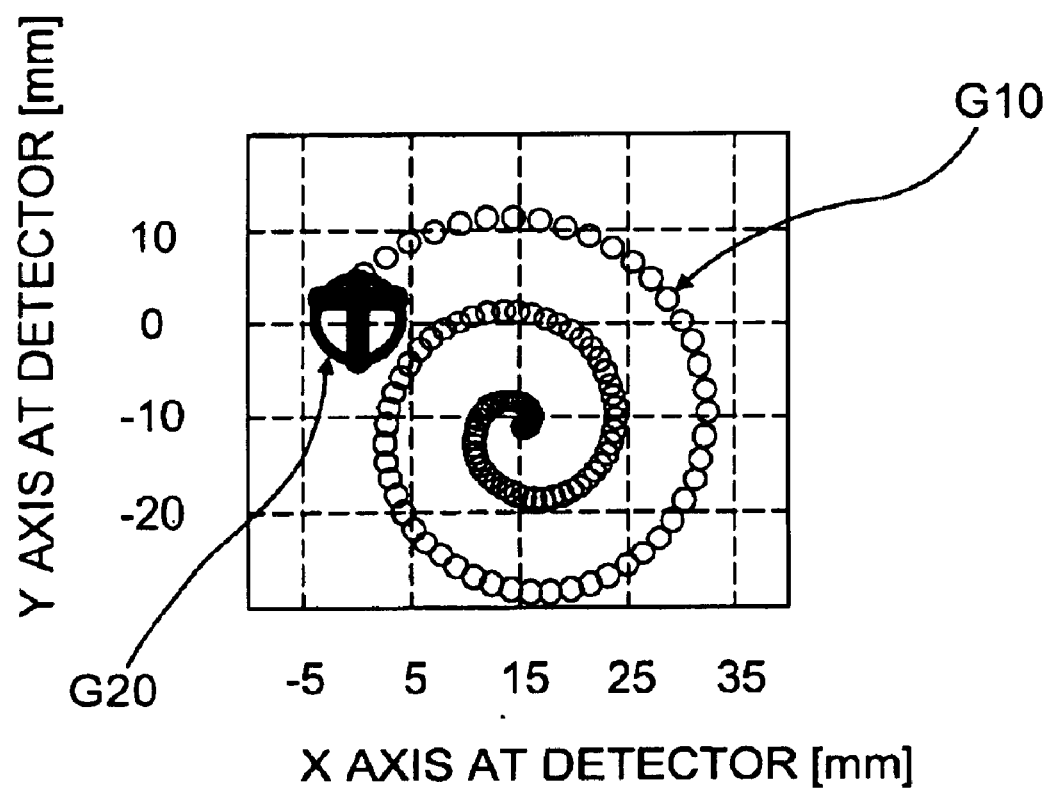
FIG. 13 shows a trajectory of the spot at the first step according to the present invention.

FIG. 13 shows a trajectory of the spot at the first step according to the present invention. Here, G10 represents the trajectory of the spot and G20 stands for detector's entrance aperture. As shown in the drawing, the spot was started from the left below side of the detector's entrance aperture and accessed spirally and centered on the detector's aperture.

Figure 14A:
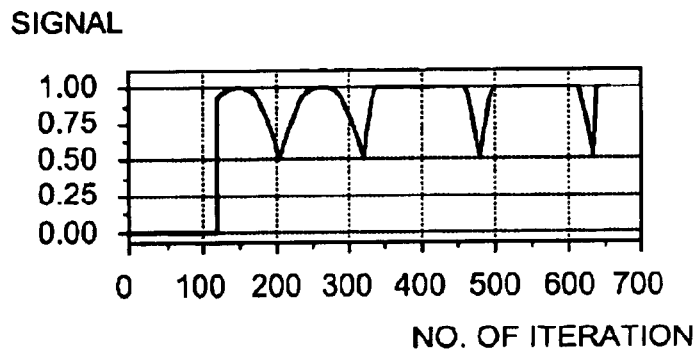
FIGS. 14A to 14D show each error and signal of detector when the ellipsometer aligns the incident angle thererof at the first step according to the present invention.
Figure 14B:
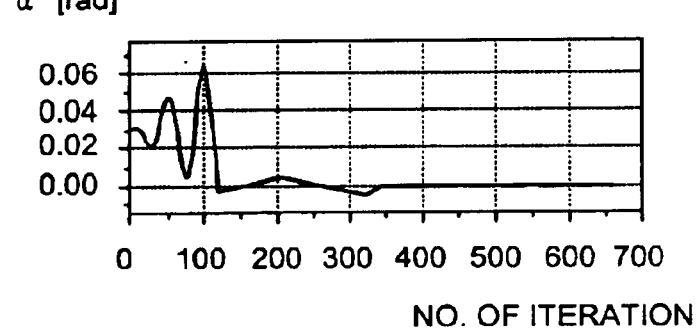
Figure 14C:
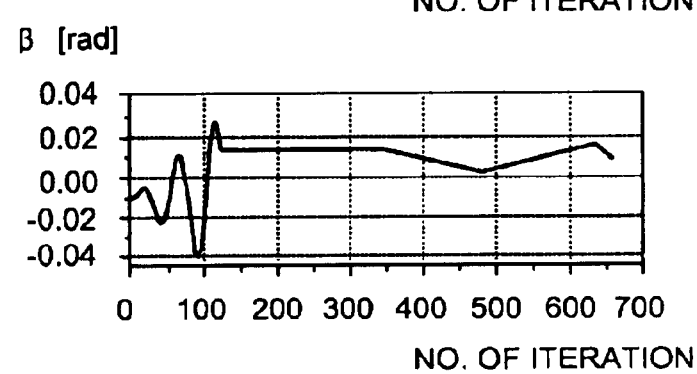
Figure 14D:
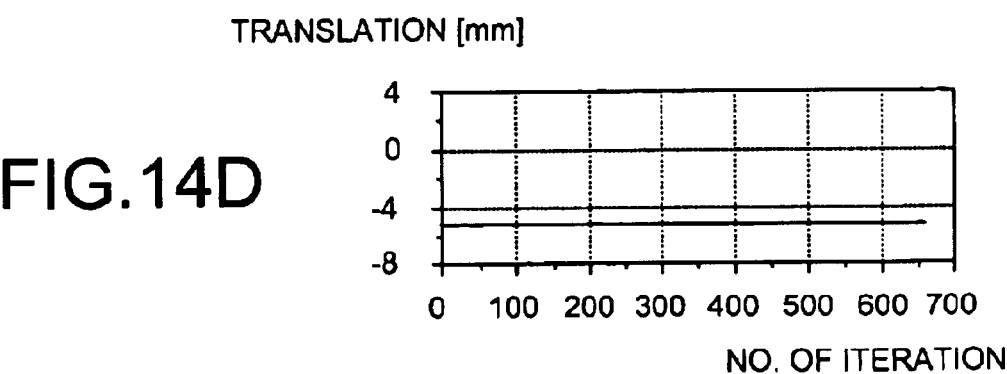

Since the incident angle was initially altered by misalignment of specimen stage, the two tilt angle errors and translation error of the specimen stage were not zero at start point as shown in FIGS. 14B to 14D. Also, The sinusoidal form interval of tilt motions indicates the accessing process of the corrective sub-step and the triangular form interval of tilt motions indicates the centering process.

The signal of detector shows the intensity of light to arrive at the detector through the entrance aperture as shown in FIG. 14D. Thus, 0 value of signal indicates that the spot is out of the detector's entrance aperture. 1 value of signal indicates that the spot is in the detector's entrance aperture. Therefore, 1 value of signal does not indicate that the detector is saturated.

On the end of the first step, the alpha tilt angle error was zero but the beta tilt angle error was not, and the translation error was unchanged.

Figure 15:
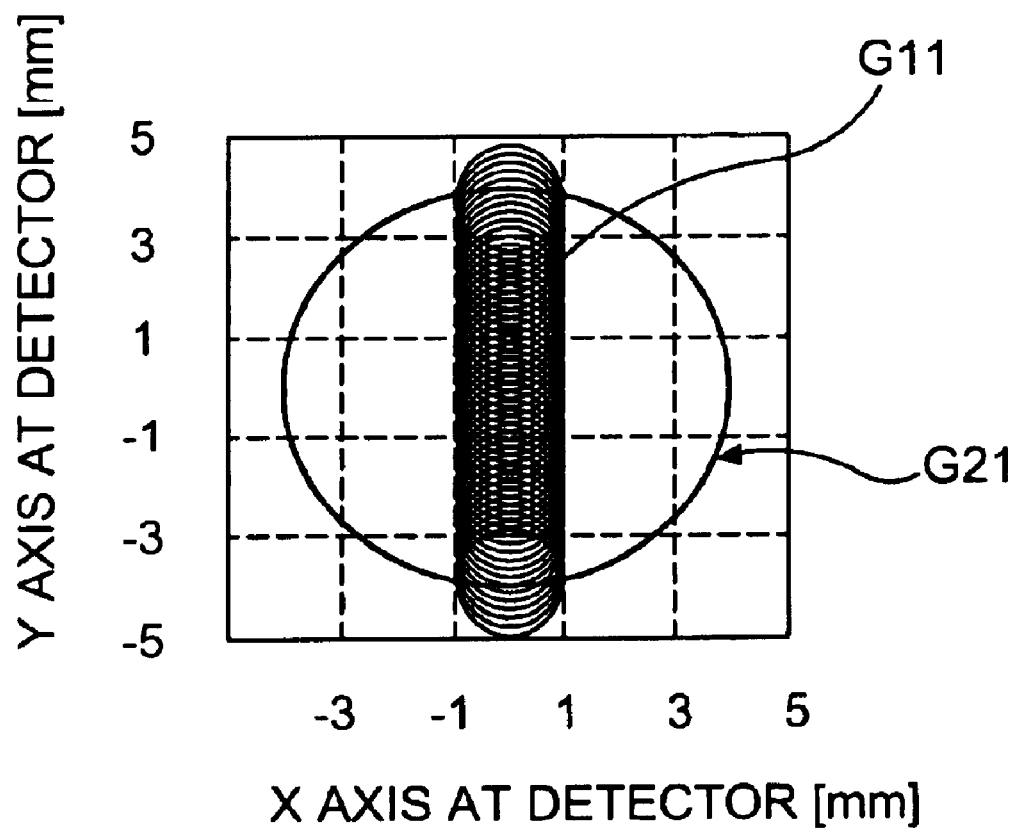
FIG. 15 shows a trajectory of the spot at the second step according to the present invention.

FIG. 15 shows a trajectory of the spot at the second step according to the present invention. Here, G11 represents the trajectory of the spot and G21 stands for detector's entrance aperture. As shown in the drawing, the spot was started from above on the center of the detector's entrance aperture and centered on. The initial position of the spot indicates that there is some translation error of specimen stage.

Figure 16A:
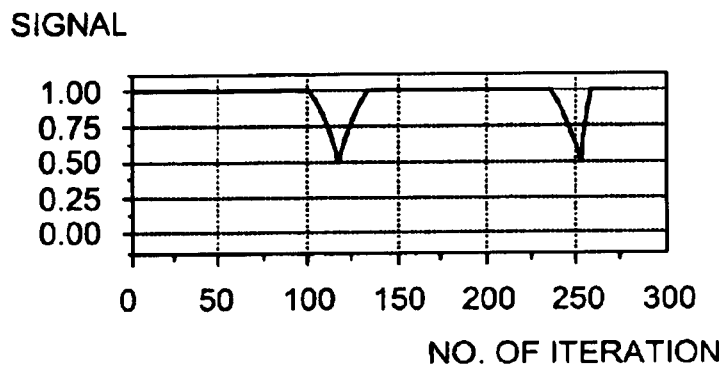
FIGS. 16A to 16D show each error and signal of detector when the ellipsometer aligns the incident angle thererof at the second step according to the present invention.
Figure 16B:
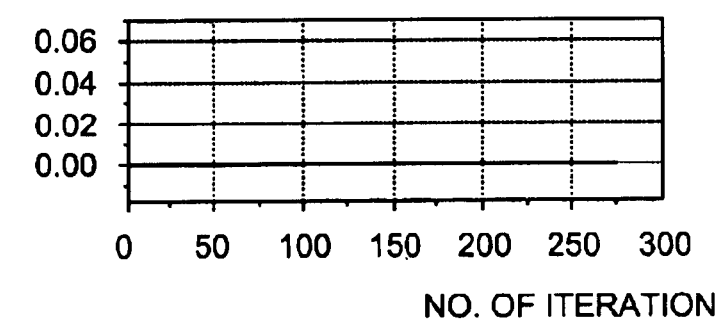
Figure 16C:
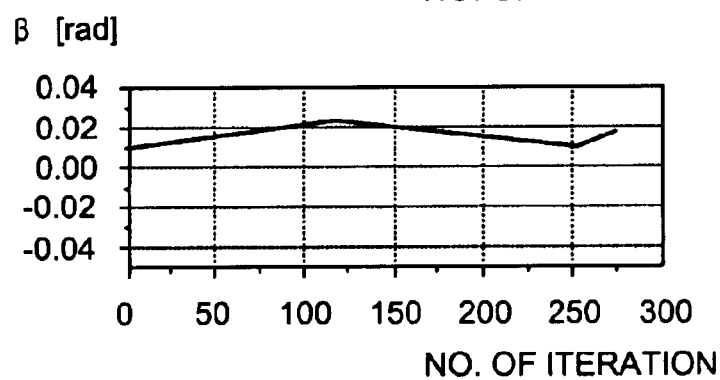

The triangular form interval of tilt motion indicates the centering process of the corrective sub-step as shown in FIGS. 16A and 16C. Since the translation error moves the spot in the incident plane, only beta tilt motion is done.

Figure 16D:
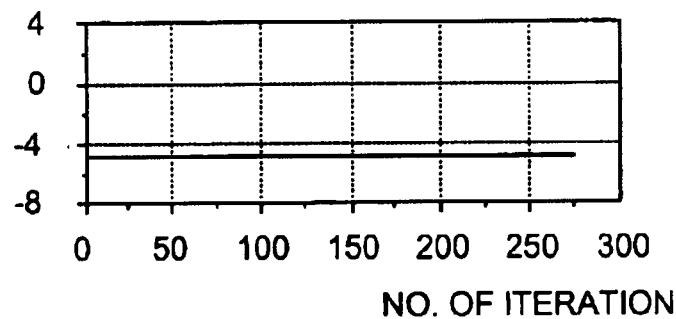

At the end of the second step, the alpha tilt angle error and translation error was unchanged, and the beta tilt angle error was changed but not zero as shown in FIGS. 16B and 16D.

Figure 17:
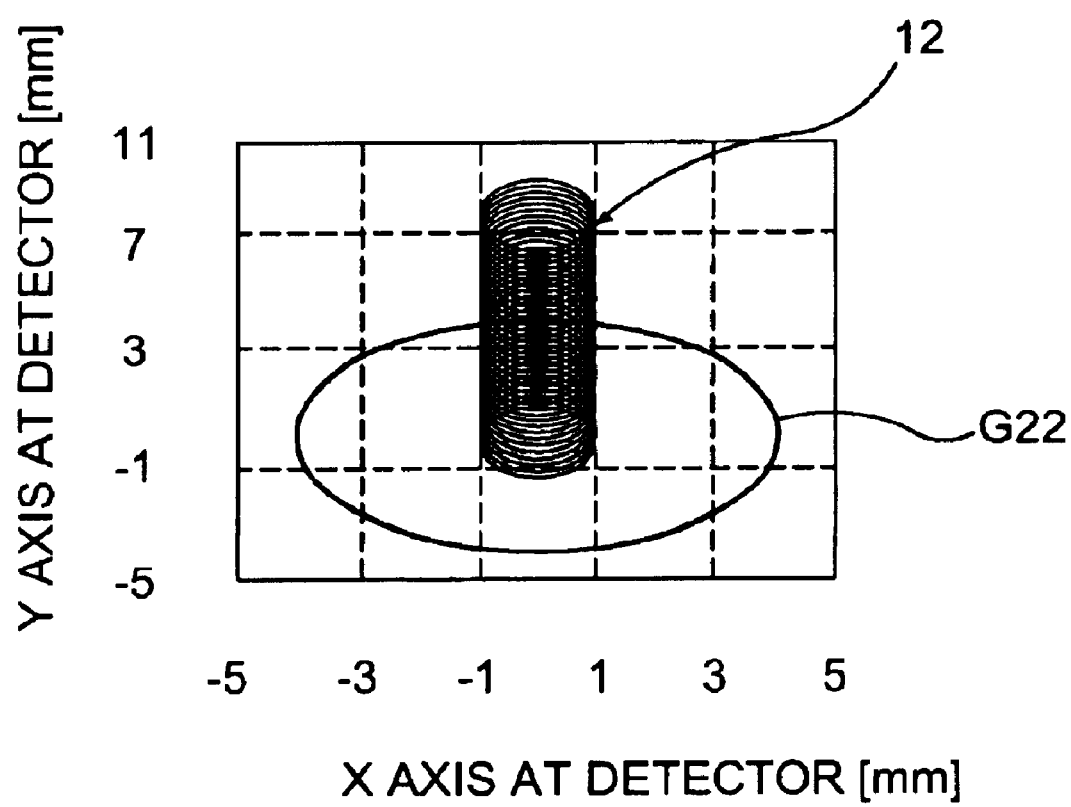
FIG. 17 shows a trajectory of the spot at the third step according to the present invention.

FIG. 17 shows a trajectory of the spot at the third step according to the A present invention. Here G12 represents the trajectory of the spot and G22 stands for detector's entrance aperture.

The translation error and the tilt angle errors were calculated with the equations (1) through (7). The translation error was eliminated earlier than the tilt angle error in FIGS. 17 and 18A to 18D.

Figure 18A:
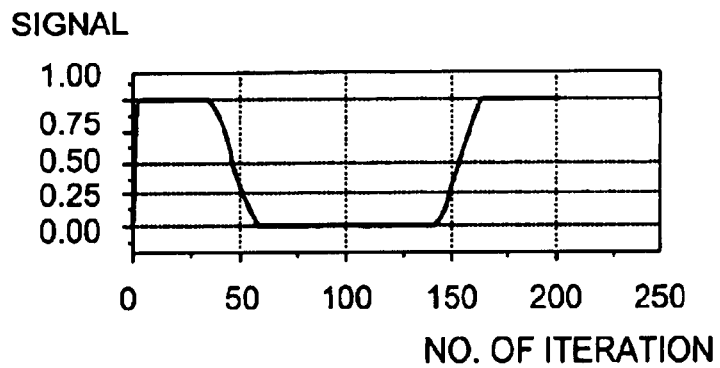
FIGS. 18A to 18D show each error and signal of detector when the ellipsometer aligns the incident angle thererof at the third step according to the present invention.
Figure 18B:
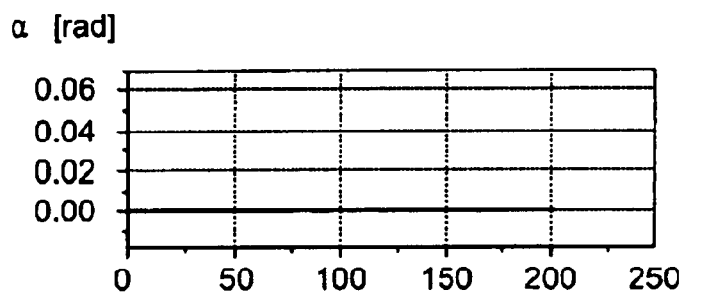
Figure 18C:
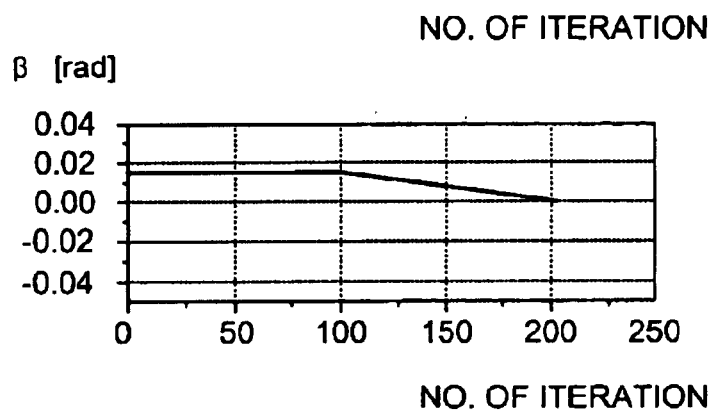
Figure 18D:
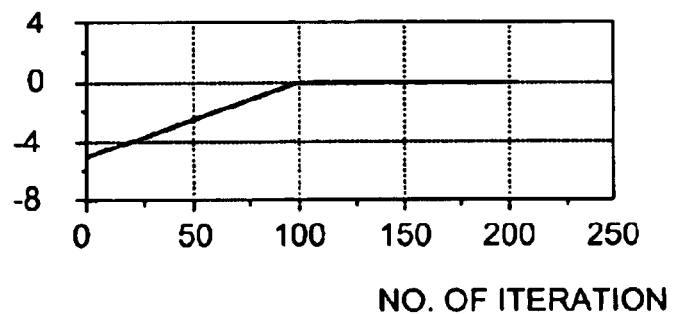

Accordingly, after ending the third step, both tilt angle errors and translation error were zero, and the signal of detector was 1 value in the FIGS. 18A to 18C. Namely, the spot was centered on the detector's entrance aperture.

FIGS. 19A to 19D show each error and signal of detector when the ellipsometer aligns the incident angle thereof according to the present invention. Here, ST1, ST2 and ST3 represent the first step, the second step and the third step of alignment algorithm, respectively and Also P1 and P2 stand for a accessing process and a centering step of the corrective sub-step, respectively.

The sinusoidal form interval of tilt motions indicates the accessing process of the corrective sub-step and the triangular form interval of tilt motions indicates the centering process. The tilt and translation motions were the same as the simulation through the three steps. The tilt angle errors and translation error started at zero and ended at some values that are the initial misaligned errors.

Figure 19A:
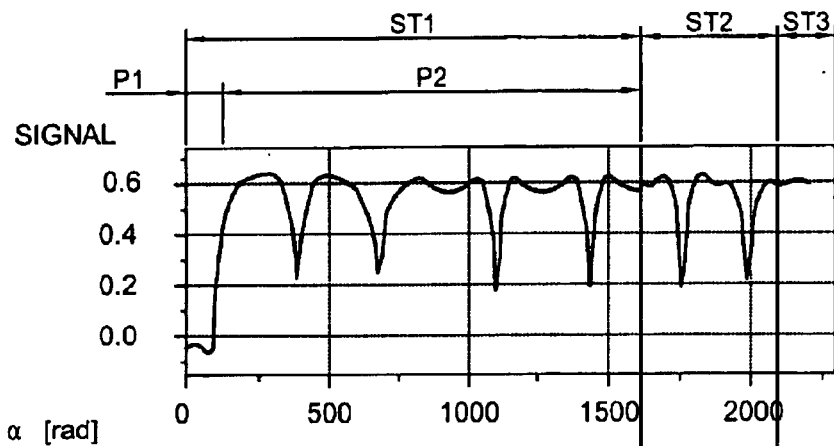
FIGS. 19A to 19D show each error and signal of detector when the ellipsometer aligns the incident angle thererof.
Figure 19B:
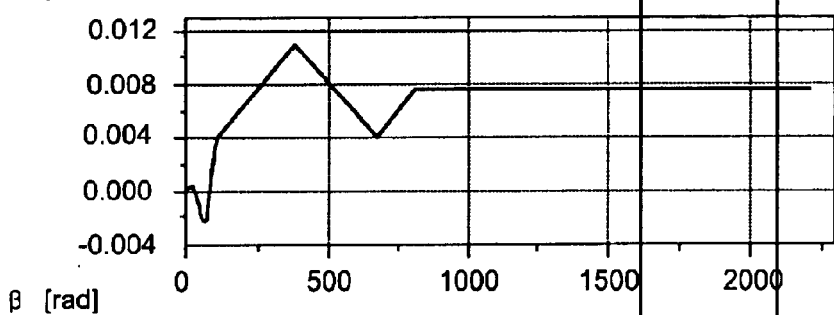
Figure 19C:
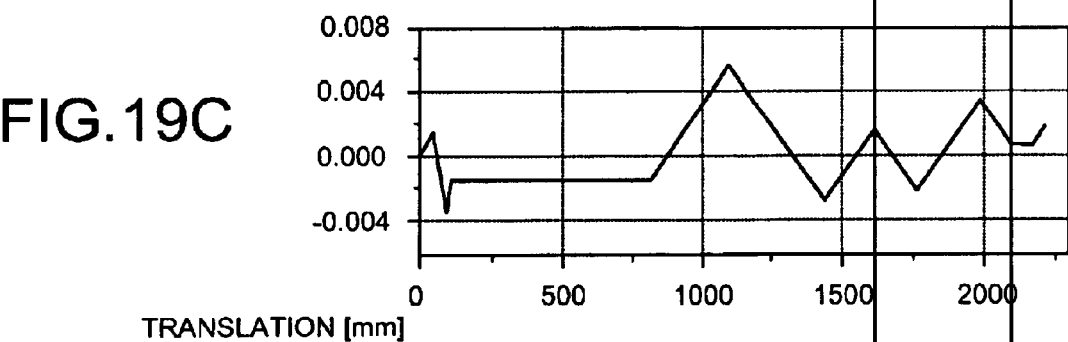
Figure 19D:
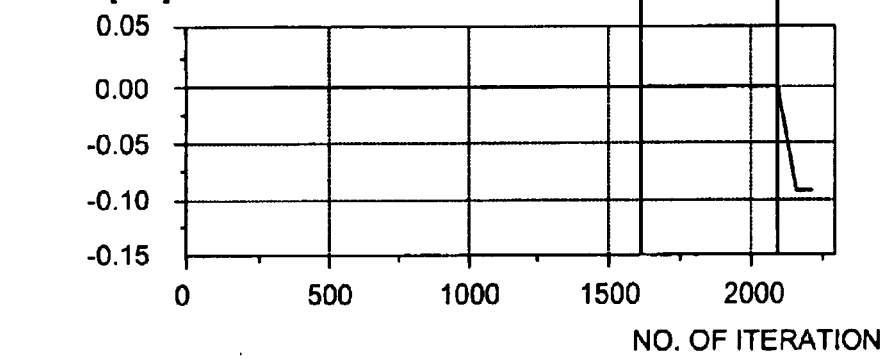

About 0 value of signal indicates that the spot is out of the detector's entrance aperture and about 0.6 value of signal indicates that the spot is in the detector's entrance aperture and the detector is not saturated in FIG. 19A. The signal showed that the detector has unexpectedly higher responsibility at the margin of the entrance aperture than at the center. But the alignment was successfully done and the experiment results were almost the same as the simulation.

Accordingly, the ellipsometer according to the present invention can easily and accurately correct the tilt angle errors and the translation error using only a 3-axis specimen stage (two tilts and one translation) and intensity at detector.

Accordingly, a 3-step auto alignment algorithm can align the incident angle of an ellipsometer using three steps and a corrective sub step.

The present invention has been embodied to an ellipsometer and a precision auto alignment method for incident angle of the ellipsometer though, it is easily appreciated that many of other alignment apparatus such as a lithograph can be modified from the present invention.

What is claimed is:

1. A precision auto alignment method for incident angle of an ellipsometer, wherein the precision auto alignment method comprises the steps of:

measuring tilt and translating angle errors according to incident angles of a polarizing unit at a first predetermined position;

compensating the errors by moving a light spot reflecting from a specimen onto a center of the detector's entrance aperture;

calculating the tilt and translating angle errors by performing said measuring and compensating steps for the polarizing unit located at a subsequent predetermined position; and correctly aligning incident angle for the ellipsometer by compensating for the calculated tilt and translating angle errors.

2. The precision auto alignment method according to claim 1, wherein the measuring step comprises:

measuring a first set of the tilt and translating errors as the light spot is centered on the detector's entrance aperture when the polarizing unit and analyzing unit are set at a first incident angle; and measuring a second set of the tilt and translating errors as the light spot is centered on the detector's entrance aperture when the polarizing unit and analyzing unit are set at a second incident angle.

3. The precision auto alignment method according to claim 1, wherein the compensating step comprises the steps of:

accessing the light spot to an entrance aperture of said detecting unit of said ellipsometer by tilting a specimen on said specimen stage of said ellipsometer; and centering the light spot to an entrance aperture of said detecting unit by obtaining a half maximum intensity and at the same time a half position between two positions having the same intensity.

4. The precision auto alignment method according to claim 3, wherein the centering step comprises the steps of:

obtaining a first center position in a X direction at a first half intensity of the first maximum intensity of between two x positions which have a first intensity; and a step of obtaining a second center position in a Y direction at a second half intensity of the second maximum intensity between two y positions which have a second intensity.

* * * * *